(12) United States Patent
Purcell et al.

(10) Patent No.: US 11,458,026 B2
(45) Date of Patent: Oct. 4, 2022

(54) DEROTATION REDUCER LINKAGE

(71) Applicant: Astura Medical Inc., Carlsbad, CA (US)

(72) Inventors: Thomas Purcell, Carlsbad, CA (US); Eric Quaal, Carlsbad, CA (US); Anthony Valkoun, Carlsbad, CA (US)

(73) Assignee: ASTURA MEDICAL INC, Irving, TX (US)

( * ) Notice: Subject to any disclaimer, the term of this patent is extended or adjusted under 35 U.S.C. 154(b) by 141 days.

(21) Appl. No.: 16/869,472

(22) Filed: May 7, 2020

(65) Prior Publication Data

US 2020/0352734 A1    Nov. 12, 2020

Related U.S. Application Data

(60) Provisional application No. 62/844,883, filed on May 8, 2019.

(51) Int. Cl.
| | |
|---|---|
| *A61B 17/70* | (2006.01) |
| *A61F 2/44* | (2006.01) |
| *A61F 2/30* | (2006.01) |

(52) U.S. Cl.
CPC ........ *A61F 2/4455* (2013.01); *A61B 17/7052* (2013.01); *A61B 17/7077* (2013.01); *A61B 2017/7073* (2013.01); *A61F 2002/30433* (2013.01); *A61F 2002/30622* (2013.01)

(58) Field of Classification Search
CPC .......... A61F 2/4455; A61F 2002/30316; A61F 2002/30621; A61B 17/7049; A61B 17/7052; A61B 2017/7073
USPC ................................ 606/250–253, 257, 278
See application file for complete search history.

(56) References Cited

U.S. PATENT DOCUMENTS

| | | | |
|---|---|---|---|
| 9,406,641 B2 | 8/2016 | Zangh et al. | |
| 2003/0018334 A1 | 1/2003 | Richelsoph et al. | |
| 2003/0114853 A1 | 6/2003 | Burgess et al. | |
| 2011/0152934 A1* | 6/2011 | Asaad ................ | A61B 17/7052 606/279 |
| 2012/0184997 A1 | 7/2012 | Simpson | |
| 2014/0163617 A1 | 6/2014 | Boachie-Adjei et al. | |

OTHER PUBLICATIONS

International Search Report and Written Opinion in PCT Application No. PCT/US2010/031946 dated Jul. 15, 2020.

\* cited by examiner

*Primary Examiner* — Eduardo C Robert
*Assistant Examiner* — Christina Negrellirodriguez
(74) *Attorney, Agent, or Firm* — Michael R. Shevlin

(57) ABSTRACT

A derotation reducer linkage with polyaxial locking connector for use with screw reducers/extenders in spinal fusion surgery.

17 Claims, 8 Drawing Sheets

DEROTATION REDUCER LINKAGE

CROSS-REFERENCE TO RELATED APPLICATIONS

This application claims the benefit of U.S. Provisional Application No. 62/844,883 filed May 8, 2019, which is incorporated herein by reference.

FIELD

The present invention relates generally to the field of surgery, and more specifically, to derotation reducer linkage for use with reducers in spinal fusion surgery.

BACKGROUND

The spine is a series of individual bones called vertebrae. A normal spine has no side-to-side curve but does have a series of front-to-back curves, giving it a gentle "S" shape. Many people have an abnormal curvature of the spine and it may be necessary to straighten or adjust the spine into a proper curvature and alignment.

Spinal surgical procedures have been developed to correct the abnormal curvature of the spine. One procedure involves placing multiple pedicle screws into the vertebrae of the curved region and coupling spinal fixation rods to the screw heads. The rods are shaped to mimic the normal curvature and force the spine into proper alignment once positioned within the screw head. The rods are then secured or locked to the screws maintain the curvature.

The Spinal surgical procedures can require complex movement and manipulation of the vertebrae to restore normal curvature to the patient. The manipulation may include a rotational force applied on pedicle screws in the coronal plane (medial-laterally) is referred to as "derotation". This is usually done by applying compression and/or distraction forces of a derotation instrument to vertebrae via the screw extenders.

It may be desirable to rigidly link reducers together to form a construct that may be rotated as one body.

Accordingly, there remains a need for instruments and methods that provide solutions to the problems of current systems. The present invention is directed toward meeting these needs.

SUMMARY

The present invention is directed to a derotation reducer linkage having a left reducer linkage having a left hook feature with a U-shaped opening sized to fit a screw reducer or extender, a left extended shaft portion and a rotatable flipper proximate an entrance to the U-shaped opening; a right reducer linkage having a right hook feature with a U-shaped opening sized to fit a screw reducer or extender, a right extended shaft portion, and a rotatable flipper proximate an entrance to the U-shaped opening, and; a locking portion coupled to the left and right extended shaft portions, the locking portion configured to allow polyaxial movement between the left and right extended shaft portions.

DETAILED DESCRIPTION

Figure 1:
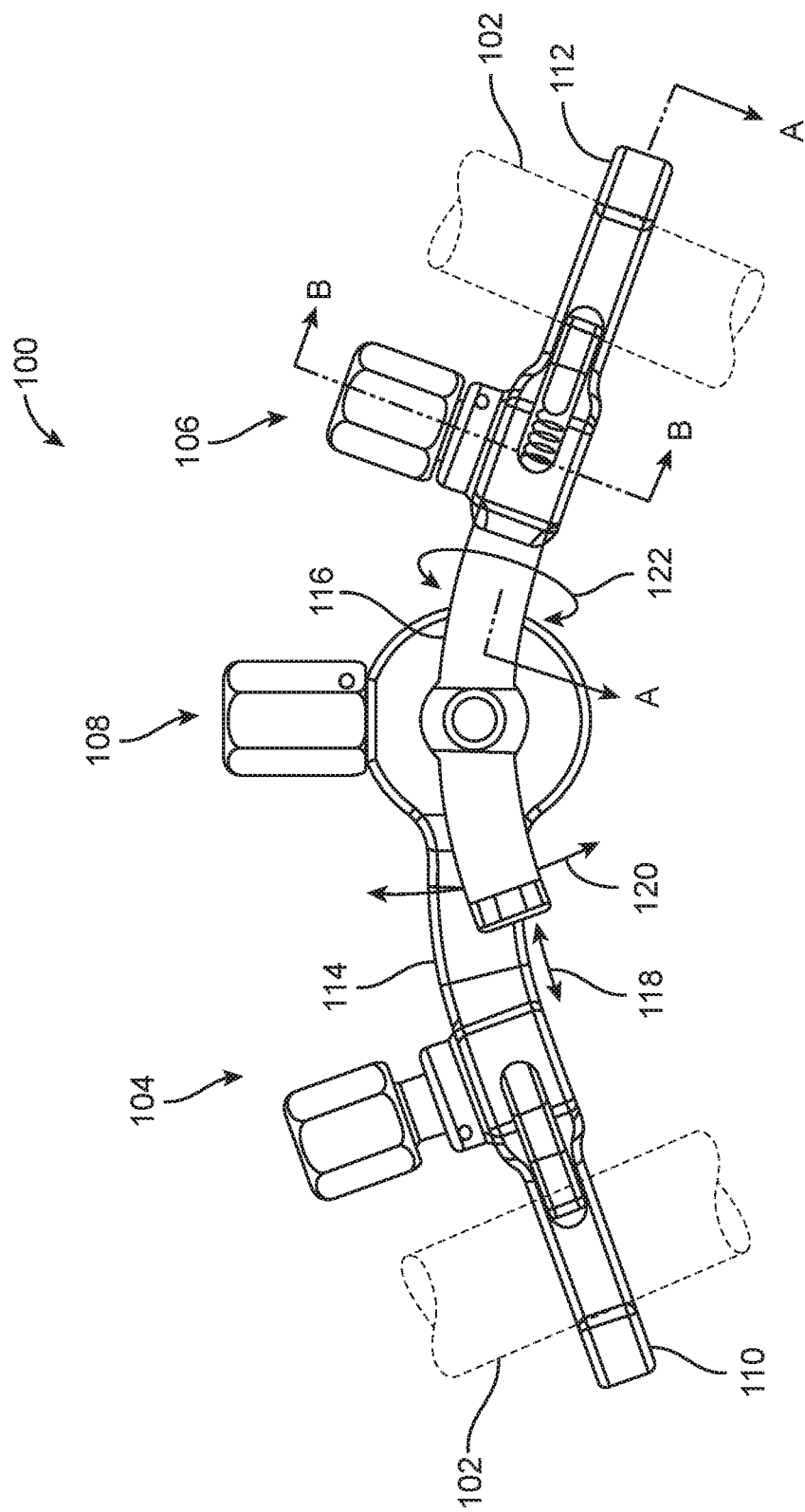
FIG. 1 shows one embodiment of a derotation reducer linkage.

Reference will now be made in detail to the present embodiments of the technology, examples of which are illustrated in the accompanying drawings. Similar reference numbers may be used to refer to similar components. However, the description is not intended to limit the present disclosure to particular embodiments, and it should be construed as including various modifications, equivalents, and/or alternatives of the embodiments described herein.

It will be understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

The expression "configured (or set) to" used in the present disclosure may be used interchangeably with, for example, the expressions "suitable for", "having the capacity to", "designed to", "adapted to", "made to" and "capable of" according to a situation. The expression "configured (or set) to" does not mean only "specifically designed to" in hardware. Alternatively, in some situations, the expression "a device configured to" may mean that the device "can" operate together with another device or component.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

FIG. 1 shows a front view of one embodiment of a derotation reducer linkage 100 that is configured to rigidly couple with spinal screw reducers or extenders 102, such as sequential screw reducers, to correct a rotation deformity of the spine by turning or rotating the deformed spine structure toward a normal position. The spine derotation reducer 100 includes a left reducer linkage 104, a right reducer linkage 106, and a locking connector 108. The left and right reducer linkage 104, 106 include left and right hook features 110, 112 with extended shaft portions or rods 114, 116 coupled to the locking connector 108.

The locking connector 108 is configured to allow the extended shaft portion 114a to move with respect to the other extended shaft portion 116a. For example, in some embodiment the housing may allow extended shaft portion 116 to translate laterally 118 with respect to the other extended shaft portion 114 to lengthen or shorten the lateral distance between the left and right hook features 110, 112. In some embodiments the housing may allow the extended shaft portions 114, 116 to rotate 120 with respect to each other to change the superior/inferior angle between the left and right hook features 110, 112. In some embodiments the housing may allow the extended shaft portions 114, 116 to rotate 122 with respect to each other to change the anterior/posterior angle between the left and right hook features 110, 112.

In use, the reducers or extenders 102 in the left and right hook features 110, 112 are manipulated to desired or optimal position, then locking connector 108 is configured to lock the extended shaft portions 114, 116 together to hold the derotation reducer linkage 100 and reducers or extenders 102 in a rigid structure or construct. Once locked, the entire spine derotation reducer linkage 100 and reducers 102 construct may be rotated or moved as one body to correct the deformity.

Figure 2:
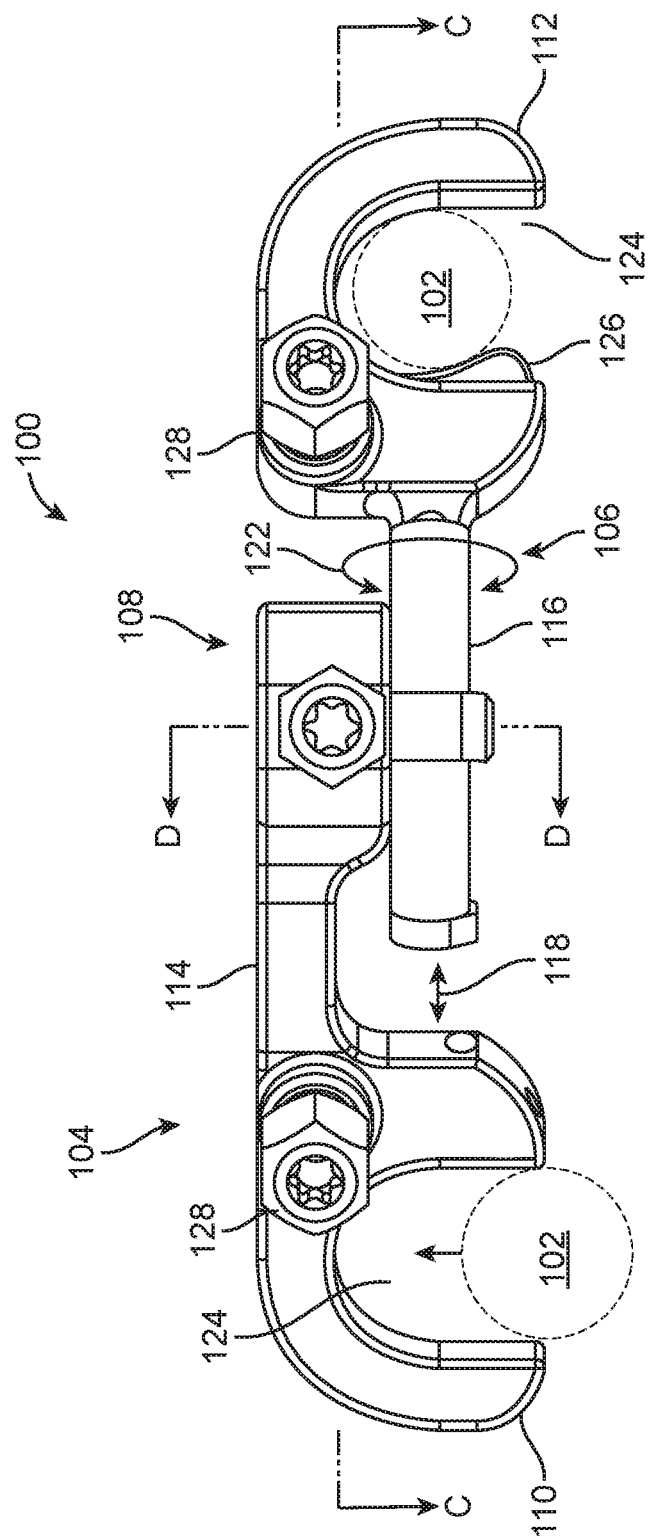
FIG. 2 shows a top view of the derotation reducer linkage.

FIG. 2 is a top view of the derotation reducer linkage 100 showing the left reducer linkage 104 with extended shaft portion or rod 114, the right reducer linkage 106 with extended shaft portion or rod 116, and the locking connector 108 configured to rotatably couple the extended shaft portions or rods 114, 116 in relation to each other. The left and right hooks 110, 112 include a U-shaped opening 124 configured to receive and hold the reducer 102. One or more flippers 126 are positioned proximate the open end or entrance of the U-shaped opening 124.

In some embodiments, the flippers 126 are coupled to wedge screws 128 configured to lock/unlock the flipper 126 in the desired position. The flippers 126 are normally positioned within the U-shaped opening 124, blocking a part of the open end or entrance. The flippers 126 are configured to rotate to unblock the entrance of the open end to allow insertion of the reducer 102. The flipper 126 may rotate with an applied pressure or force, or may be self-distracting, such as upon contact with the reducer 102. Once the reducer 102 is within the opening 124, the wedge screw 128 is tightened to lock the flipper 126 in the opening.

To hold the reducers 102, the flippers 126 move or rotate to allow the reducer 102 to enter the U-shaped opening 124, shown in FIG. 2 entering left hook 110. Once the reducers 102 is in position, the flippers 126 move or rotate back to block the open end so the reducers do not come out of U-shaped opening 124, shown in FIG. 2 within right hook 112. The wedge screws 128 are then tightened to force the flippers 126 against the reducers 102 and lock the reducers in the left and right hooks 110, 112.

Figure 3:
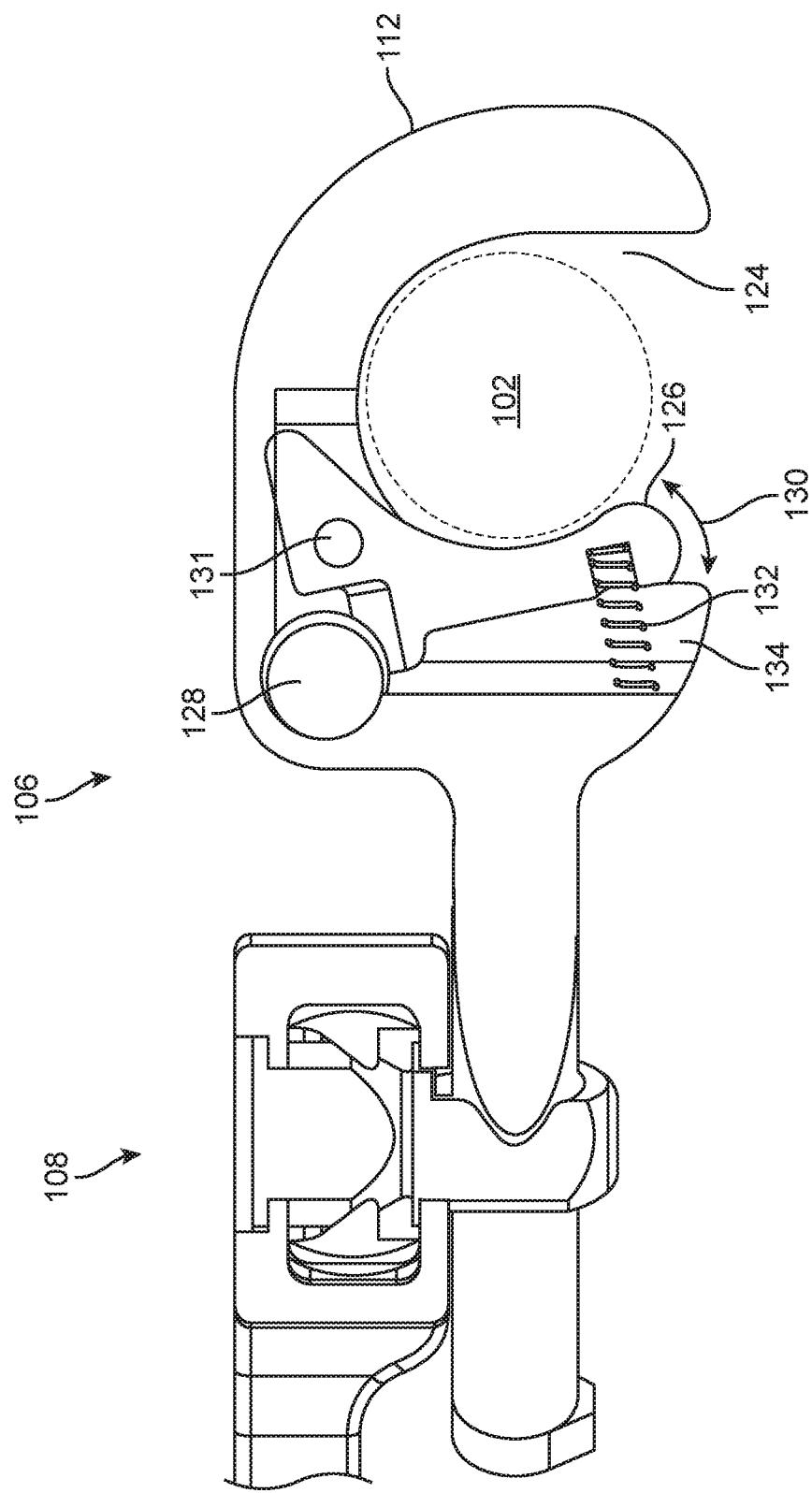
FIG. 3 is a sectional view at A-A of FIG. 1.
Figure 4:
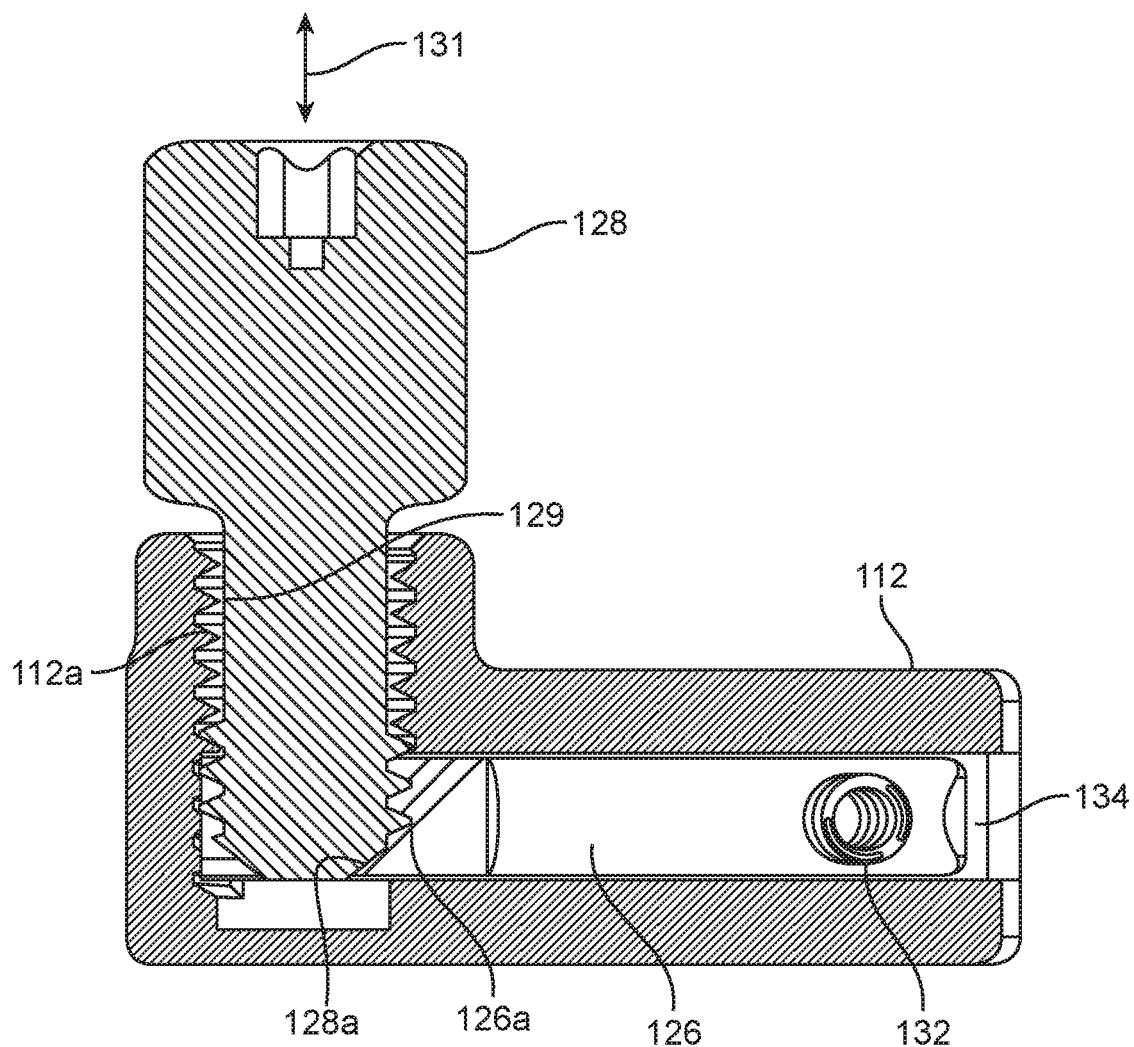
FIG. 4 is a sectional view at B-B of FIG. 1.

FIG. 3 is a sectional view at A-A of FIG. 1 and FIG. 4 is a sectional view at B-B of FIG. 1 showing details of the right hook 112 and flipper 126. This description also applies to the left hood 110. In the embodiment shown, the wedge screw 128 is configured to engage the flipper 126 to lock the flipper 126 in the closed position within the U-shaped opening 124. The wedge screw 128 includes a threaded part 129 configured to engage a threaded opening 110a, 112a of the hooks 110, 112. When the wedge screw 128 is rotated, the threaded engagement moves the wedge screw up and down 131 to lock the flipper 126 or unlock the flipper 126.

The flipper 126 is normally positioned within the U-shaped opening 124 blocking a part of the open end or entrance. The flipper 126 is designed to rotate 130 on a pivot pin 131 to unblock the entrance of the open end to allow insertion of the reducer 102. A spring 132 may be coupled to the flipper 126 to hold the flipper 126 in the normal or closed position, and also assist the flipper 126 back into the normal or closed position after flipper 126 rotation to allow insertion of the reducer 102. The springs 132 may be any spring that will allow the flipper to rotate have enough force to return the flipper to the normal position after rotation. In the embodiment shown, the left and right hook features 110, 112 include recesses, openings or pockets 134 sized to fit the flipper 126 when it is rotated out of the opening 124. Once the reducer 102 is fully seated within opening 124, the flippers 126 may then return into the opening. In the embodiment shown, the flipper 126 includes a ramped portion 126a that engages the tapered end 128a of the wedge screw 128. When the wedge screw 128 is tightened, the tapered end 128a slides down the ramped portion 126a to push the flipper 126 in the opening and engagement with the reducer 102, thereby locking the reducer within the right hook and prevent the reducer 102 from being removed.

Figure 5:
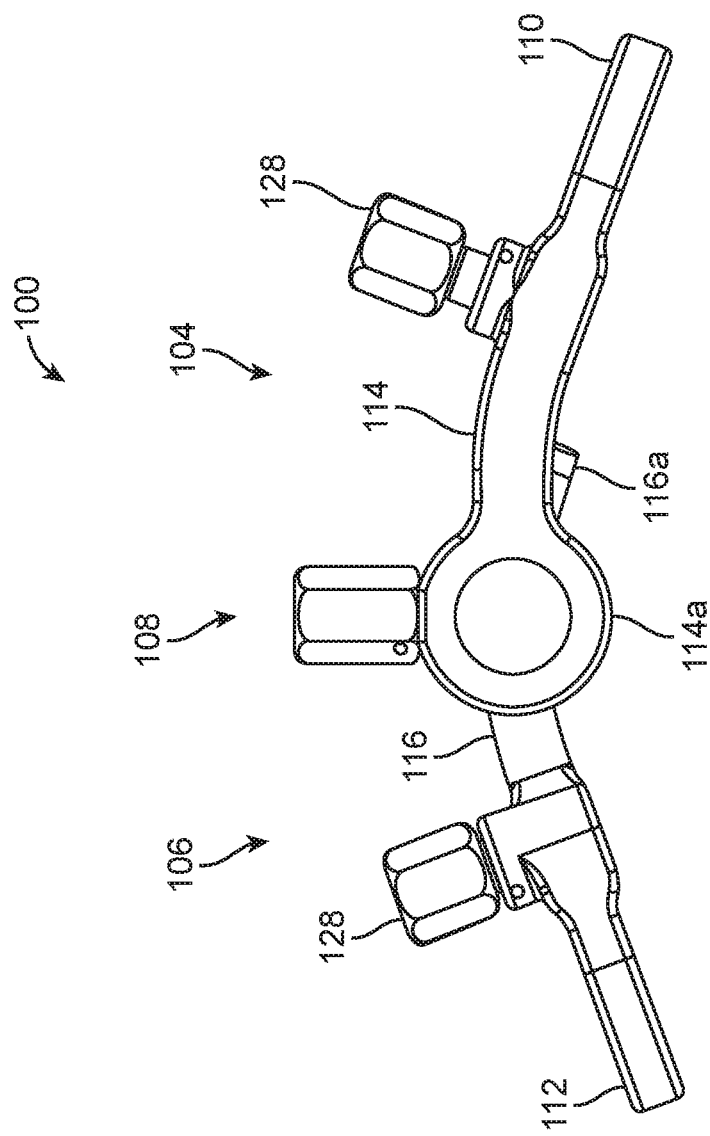
FIG. 5 shows a rear view of the derotation reducer linkage 100.

FIG. 5 shows a rear view of the derotation reducer linkage 100 that includes the left reducer linkage 104 with extended shaft portion or rod 114, the right reducer linkage 106 with extended shaft portion or rod 116, and the locking connector 108 that rotatably couples the extended shaft portions or rods 114, 116 in relation to each other.

Figure 6:
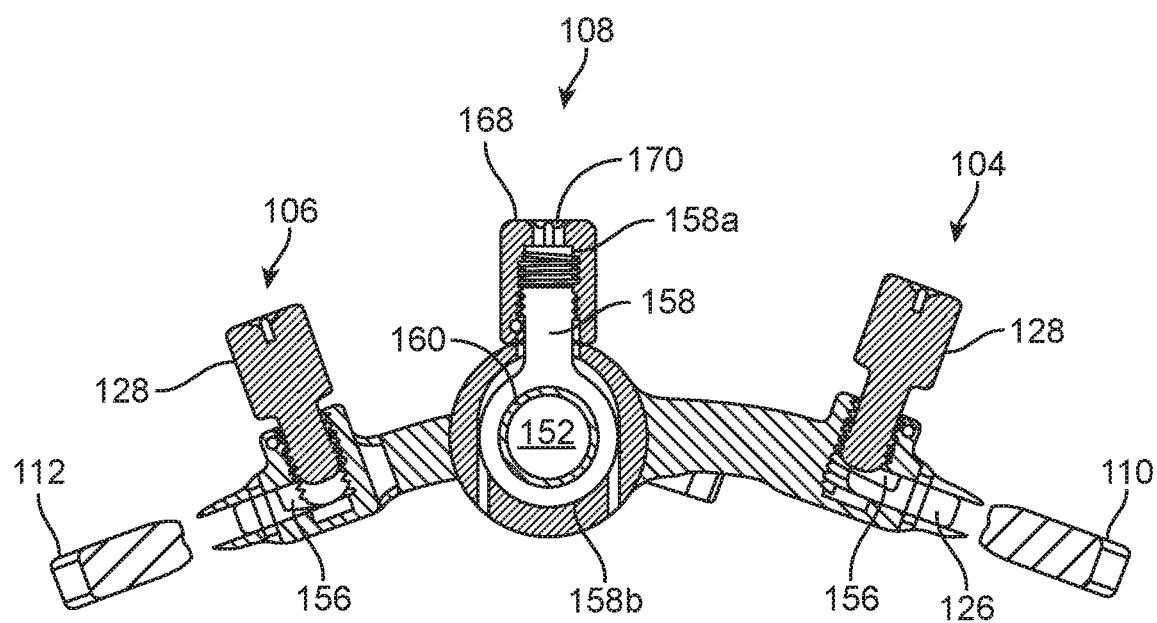
FIG. 6 is a sectional view at C-C of FIG. 2.
Figure 7:
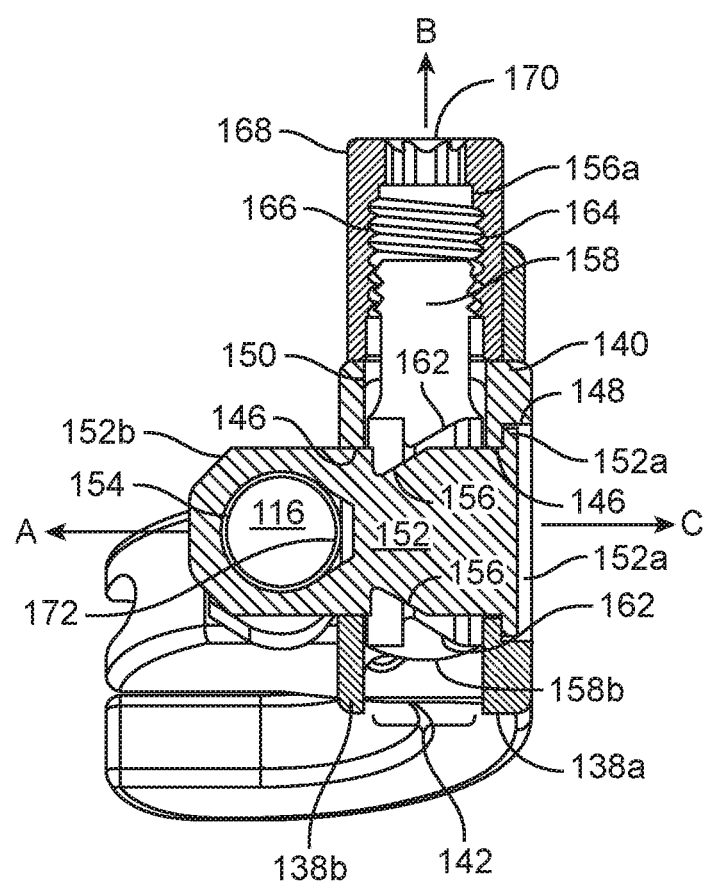
FIG. 7 is a sectional view at D-D of FIG. 2.

FIG. 6 is a sectional view at C-C of FIG. 2, and FIG. 7 is a sectional view at D-D of FIG. 2 showing internal details of the locking connector 108 and left and right extended shaft portions 114a, 116a. As discussed above, the locking connector 108 is a polyaxial connector to allow the left and right hooks 110, 112 to rotate in the lateral direction, anterior/posterior direction, and superior/inferior direction in relation to each other. The locking connector 108 is configured to engage the extended shaft portions 114, 116 of left and right reducer arms 104, 106 to allow the polyaxial rotation, then lock the extended shaft portions 114, 116 in the desired position, thereby locking the left and right hooks 110, 112 in the desired position.

In the embodiment shown, the extended shaft portion 114a includes a clevis portion 138 having first and second sides 138a and 138b, a closed top portion 140 and an open bottom portion 142 forming a cavity 144 between the first and second sides 138a, 138b. A first hole or bore 146 extends through the first and second sides 138a, 138b and a coaxial counterbore hole 148 is positioned in an outer surface of the first side 138a. A second hole 150 extends through the closed top portion 140.

The locking connector 108 includes a locking connector cylinder 152 coupled to the locking connector eye bolt 158 with a locking nut or cap 168. When the locking nut or cap 168 is rotated, the locking connector eye bolt 158 is configured to lock/unlock the locking connector cylinder 152. The locking connector cylinder 152 includes a first end 152a sized to fit through the first and second holes 146, 148, and a flanged second end 152b sized to engage the coaxial counterbore hole 148. The first end 152a also includes a rod hole 154 sized for insertion of the end 116a of extended shaft portion or rod 116. The locking connector cylinder 152 also includes a locking connector cylinder ramp 156 configured to engage a locking connector eye bolt ramp 162 (discussed below). In the embodiment shown, the locking connector cylinder ramp 156 is part of an undercut portion of the locking connector cylinder 152.

The locking connector eye bolt 158 includes a first end 158a sized to fit through the second hole 150 in the top portion 140 and a second end 158b sized to fit within the cavity 144. The first end 158a includes a threaded portion 164 configured to engage internal threads 166 in a locking nut or cap 168. The locking nut or cap 168 may also have a tool engagement feature 170. The second end 158b includes a lock hole or bore 160 sized to fit the first end 152a of the locking connector cylinder 152. The lock hole or bore 160 also include the locking connector eye bolt ramp 162 configured to engage the locking connector cylinder ramp 156.

To assemble locking connector 108, the locking connector eye bolt 158 is inserted into the clevis portion 138 of the extended shaft portion 114a. The first end 158a of the locking connector eye bolt 158 goes through the second hole 150 of the closed top portion 140 and the second the second end 158b is positioned within the cavity 144 (shown in FIG. 6). The locking nut or cap 168 may be loosely threaded on the first end 158a to prevent the eye blot 158 from falling out of the cavity 144.

The lock hole or bore 160 in the locking connector eye bolt 158 is then axially aligned with the first and second holes 146, 148. The first end 152a of locking connector cylinder 152 is then inserted through the first and second holes 146, 148 and lock hole 160 in the direction of Arrow A (shown in the horizontal direction) until the flanged second end 152b engages the coaxial counterbore hole 148 preventing further movement. The extended shaft portion or rod 116a is then inserted through the rod hole 154. In some embodiments, the locking nut or cap 168 may be rotated until there is light friction between the locking connector cylinder 152, locking connector eye bolt 158 and extended shaft portion or rod 116a. The light friction should allow components to move with the application of force, and also have sufficient resistance to hold the components in position during adjustment.

Once assembled, the left and right reducer linkage 104, 106 are moved/rotated so that the left and right hook features 110, 112 are positioned in the desired position. Once in the desired position, the locking nut 168 is tightened, which moves the first end 158a of the locking connector eye bolt 158 in the direction of Arrow B (shown moving in the vertical direction). As the locking connector eye bolt 158 moves upward, the locking connector eye bolt ramp 162 slidably engages the locking connector cylinder ramp 156, moving the locking connector cylinder 152 in the direction of Arrow C. As the locking connector cylinder 152 moves in direction of Arrow C, the extended shaft portion or rod 116a is pulled into frictional engagement 172 with the second side 138b of the clevis portion 138, locking the extended shaft portion or rod 116a in place. Along with movement in the direction of Arrow A, the locking connector cylinder 152 into frictional engagement with the first and second holes 146, 148, locking the locking connector cylinder 152 in the clevis 138 to prevent any rotation. So the tightening of the locking nut 168 provides two locking features, first it locks the extended shaft portion or rod 116a to prevent lateral movement or anterior/posterior movement between the left and right hook features 110, 112, and second it locks the locking connector cylinder 152 in the clevis 138 to prevent superior/inferior movement between the left and right hook features 110, 112.

Figure 8A:
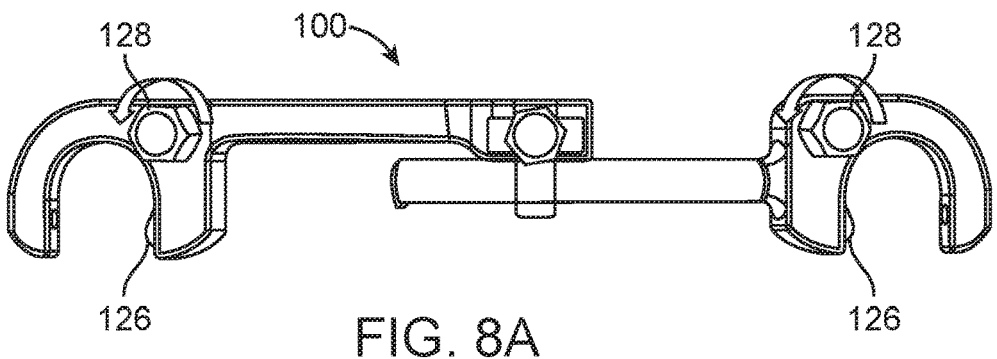
FIGS. 8A-8D are views showing assembly of the derotation reducer linkage and screw reducer/extender construct.
Figure 8B:
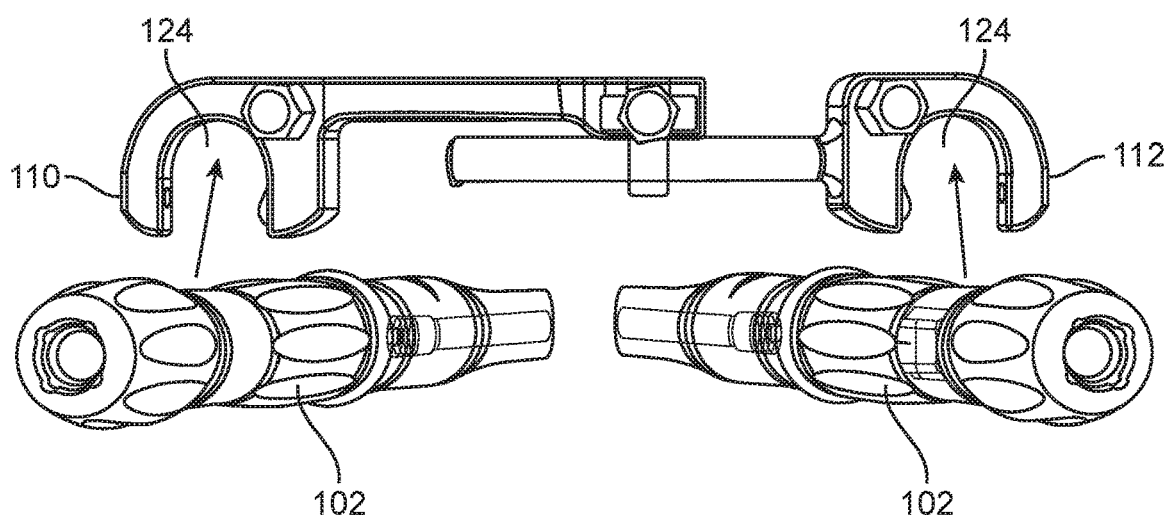
Figure 8C:
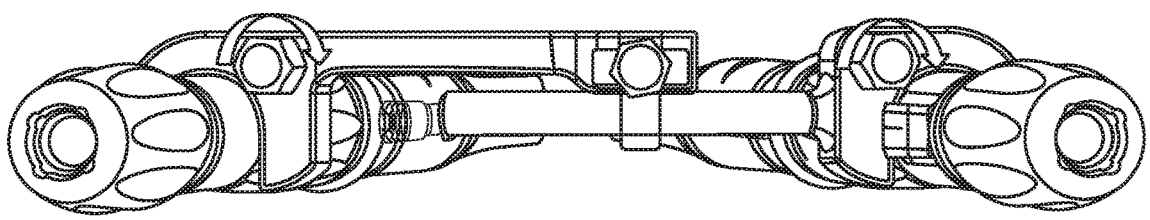
Figure 8D:
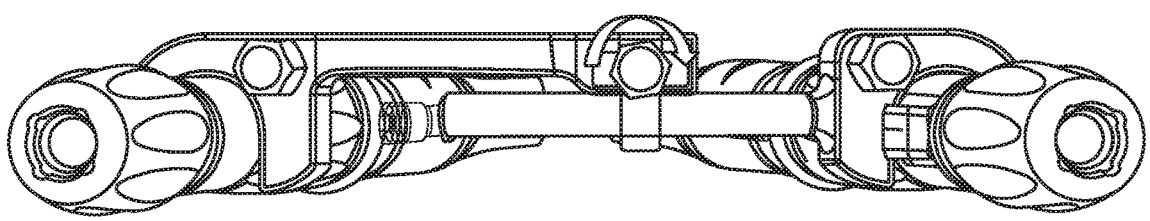

FIGS. 8A-8D show assembly of the derotation reducer linkage 100 and screw reducer/extender 102. In FIG. 8A, the wedge screws 128 are rotated to allow rotation of the flippers 126. FIG. 8B shows insertion of the reducer/extenders 102 inserted into the U-shaped openings 124 of the left and right hook features 110, 112. As discussed above, the flippers 126 are configured to rotate 130 to allow passage of the reducer/extender 102 into the U-shaped channel 124. Once the screw reducer 102 is fully seated in the U-shaped channel 124, the flipper 126 rotates back into position to block the opening 124. The wedge screw 128 is then rotated to push the flipper 126 into contact with the reducer/extender 102 and lock the flipper 102 in the left and right hook features 110, 112, see FIG. 8C. The reducer/extenders 102 are then moved to the desired position by moving the left and right hook features 110, 112. As discussed above, the locking connector 108 allows polyaxial movement between the left and right hook features 110, 112, including lateral movement, anterior/posterior movement, and/or superior/inferior movement. Once locked, the entire spine derotation reducer linkage 100 and reducers 102 construct may be rotated or moved as one body to correct the deformity.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. A derotation reducer device for spinal fusion surgery comprising:
    a left reducer linkage having a left hook feature with an opening sized to fit a screw reducer or extender, a left extended shaft portion and a left flipper blocking part of the opening and being configured to rotate to unblock the opening to allow insertion of the screw reducer or extender into the opening, and once the screw reducer or extender are within the opening, to rotate back to block the opening and lock the screw reducer or extender within the opening;
    a right reducer linkage having a right hook feature with an opening sized to fit a screw reducer or extender, a right extended shaft portion, and a right flipper blocking part of the opening and being configured rotate to unblock the opening to allow insertion of the screw reducer or extender into the opening, and once the screw reducer or extender are within the opening, to rotate back to block the opening and to lock the screw reducer or extender within the opening, and;
    a locking portion coupled to the left and right extended shaft portions, the locking portion configured to allow polyaxial movement between the left and right extended shaft portions and left and right hook features.

2. The device of claim 1, wherein
the left extended shaft portion includes a clevis portion; and
the locking portion includes:
  a locking connector eye bolt configured to couple with the clevis portion;
  a locking nut or cap coupled to the locking connector eye bolt; and
  a locking connector cylinder having a lock hole sized for insertion of the left extended shaft portion;
wherein the locking connector cylinder is configured to couple with the clevis portion, the locking connector eye bolt, and the left extended shaft portion;
wherein when the locking nut or cap is rotated, the locking connector eye bolt is configured to:
  lock the left extended shaft portion to prevent lateral movement or anterior/posterior movement between the left and right hook features; and
  lock the locking connector cylinder in the clevis portion to prevent superior/inferior movement between the left and right hook features.

3. The device of claim 2, wherein the lock hole includes a locking connector eye bolt ramp, and the locking connector cylinder includes a locking connector cylinder ramp, wherein the locking connector eye bolt ramp is configured to slidably engage the locking connector cylinder ramp to move the lock connector cylinder.

4. The device of claim 2, wherein the clevis portion includes first and second sides, a closed top portion and an open bottom portion forming a cavity between the first and second sides, and a first hole extends through the first and second sides and a coaxial counterbore hole is positioned in an outer surface of the first side, and a second hole extends through the closed top portion; and
  the locking connector eye bolt includes a first end sized to fit through the second hole in the top portion and a second end being sized to fit within the cavity.

5. The device of claim 1, wherein:
  the left and right flippers are configured to rotate and unblock the openings upon contact with the screw reducer or extender.

6. The device of claim 1, wherein polyaxial movement includes:
  medial/lateral movement includes movement between the left reducer linkage and right reducer linkage to lengthen or shorten a lateral distance between the left and right hook features;
  anterior/posterior movement includes angular movement between the left and right extended shaft portions to change an angle between the left and right extended shaft portion; and
  superior/inferior movement includes rotational movement between the left and right extended shaft portions to change an angle between the left and right hook features.

7. A derotation reducer device for spinal fusion surgery comprising:
  a left reducer linkage having a left hook feature with a left extended shaft portion, the left hook feature having an opening and a left flipper being configured to couple with a screw reducer or extender, the left flipper blocking part of the opening and being configured to rotate to unblock the opening to allow insertion of the screw reducer or extender into the opening, and once the once the screw reducer or extender are within the opening, to rotate back to block the opening;
  a right reducer linkage having a right hook feature with a right extended shaft portion, the right hook feature having an opening and a right flipper being configured to couple with a screw reducer or extender, the right flipper blocking part of the opening and being configured to rotate to unblock the opening to allow insertion of the screw reducer or extender into the opening, and once the screw reducer or extender are within the opening, to rotate back to block the opening; and
  a locking portion coupled to the left and right extended shaft portions, the locking portion configured to allow polyaxial movement between the left and right extended shaft portions and left and right hook features.

8. The device of claim 7, wherein
the left extended shaft portion includes a clevis portion; and
the locking portion includes:
  a locking connector eye bolt configured to couple with the clevis portion;
  a locking nut or cap coupled to the locking connector eye bolt; and
  a locking connector cylinder having a lock hole sized for insertion of the left extended shaft portion;
wherein the locking connector cylinder is configured to couple with the clevis portion, the locking connector eye bolt, and the left extended shaft portion;
wherein when the locking nut or cap is rotated, the locking connector eye bolt is configured to:
  lock the left extended shaft portion to prevent lateral movement or anterior/posterior movement between the left and right hook features; and
  lock the locking connector cylinder in the clevis portion to prevent superior/inferior movement between the left and right hook features.

9. The device of claim 8, wherein the lock hole includes a locking connector eye bolt ramp, and the locking connector cylinder includes a locking connector cylinder ramp, wherein the locking connector eye bolt ramp is configured to slidably engage the locking connector cylinder ramp to move the lock connector cylinder.

10. The device of claim 8, wherein the clevis portion includes first and second sides, a closed top portion and an open bottom portion forming a cavity between the first and second sides, and a first hole extends through the first and second sides and a coaxial counterbore hole is positioned in an outer surface of the first side, and a second hole extends through the closed top portion.

11. The device of claim 10, wherein the locking connector eye bolt includes a first end sized to fit through the second hole in the top portion and a second end being sized to fit within the cavity.

12. The device of claim 7, wherein
the left flipper is configured to lock the screw reducer or extender within the left hook feature opening, and the right flipper is configured to lock the screw reducer or extender within the right hook feature opening.

13. The device of claim 7, wherein polyaxial movement includes:
  medial/lateral movement between the left reducer linkage and right reducer linkage to lengthen or shorten a lateral distance between the left and right hook features;
  anterior/posterior angular movement between the left and right extended shaft portions to change an angle between the left and right extended shaft portion; and superior/inferior rotational movement between the left and right extended shaft portions to change an angle between the left and right hook features.

14. A derotation reducer device for spinal fusion surgery comprising:
   a left reducer linkage having a left extended shaft portion with a clevis portion, the left reducer linkage includes a left hook feature with an opening sized to fit a screw reducer or extender and a left flipper blocking part of the opening being configured to rotate to unblock the opening to allow insertion of the screw reducer or extender into the opening, and once the once the screw reducer or extender are within the opening, to rotate back to couple with a screw reducer or extender and block the opening;
   a right reducer linkage having a right extended shaft portion, the right reducer linkage includes a right hook feature with an opening sized to fit a screw reducer or extender being configured to rotate to unblock the opening to allow insertion of the screw reducer or extender into the opening, and once the once the screw reducer or extender are within the opening, to rotate back to couple with a screw reducer or extender and block the opening, and
   a locking portion coupled to the left and right extended shaft portions, the locking portion configured to allow polyaxial movement between the left and right extended shaft portions, the locking portion includes:
      a locking connector eye bolt configured to couple with the clevis portion;
      a locking nut or cap coupled to the locking connector eye bolt; and
      a locking connector cylinder having a lock hole sized for insertion of the left extended shaft portion;
   wherein the locking connector cylinder is configured to couple with the: clevis portion; the locking connector eye bolt; and the left extended shaft portion;
   wherein when the locking nut or cap is rotated, the locking connector eye bolt is configured to:
      lock the left extended shaft portion to prevent lateral movement or anterior/posterior movement between the left and right reducer linkages; and
      lock the locking connector cylinder in the clevis portion to prevent superior/inferior movement between the left and right reducer linkages.

15. The device of claim 14, wherein the lock hole includes a locking connector eye bolt ramp, and the locking connector cylinder includes a locking connector cylinder ramp, wherein the locking connector eye bolt ramp is configured to slidably engage the locking connector cylinder ramp to move the lock connector cylinder.

16. The device of claim 14, wherein the clevis portion includes first and second sides, a closed top portion and an open bottom portion forming a cavity between the first and second sides, and a first hole extends through the first and second sides and a coaxial counterbore hole is positioned in an outer surface of the first side, and a second hole extends through the closed top portion.

17. The device of claim 16, wherein the locking connector eye bolt includes a first end sized to fit through the second hole in the top portion and a second end being sized to fit within the cavity.

* * * * *